[19] United States Patent
Hampar et al.

[11] 4,430,437
[45] Feb. 7, 1984

[54] **TEST METHODS EMPLOYING MONOCLONAL ANTIBODIES AGAINST *HERPES SIMPLEX* VIRUS TYPES 1 AND 2 NUCLEOCAPSIDS PROTEINS**

[75] Inventors: Berge Hampar, Middletown; Martin Zweig, Walkersville; Harvey Rabin, Braddock Heights, all of Md.; Conrad J. Heilman, Jr., Chester, N.Y.; Ralph F. Hopkins, III; Russell H. Neubauer, both of Frederick, Md.

[73] Assignee: The United States of America as represented by the Department of Health and Human Services, Washington, D.C.

[21] Appl. No.: 181,954

[22] Filed: Aug. 27, 1980

[51] Int. Cl.³ .................. G01N 33/54; G01N 33/56; G01N 33/58
[52] U.S. Cl. .................... 436/548; 424/86; 424/89; 435/5; 435/7; 435/172; 435/240; 435/241; 436/536; 436/544; 436/545; 436/546
[58] Field of Search ............... 424/8, 12, 85, 86, 89; 435/5, 7, 172, 235, 239, 240, 241; 436/536, 544, 545, 546, 548

[56] References Cited
PUBLICATIONS

Koprowski, Lymph. Hybridomas, Curr. Topics in Micro & Immunol. Springer Verlag, NY, 1978, pp. 8–19.
Hampar, Herpes Virus, (Kaplan, ed.), Acad. Press, NY, 1973, Cpt. 7, pp. 221–259.
Koprowski, Proc. Natl. Acad. Sci., USA, vol. 74, Jul. 1977, pp. 2985–2988.
Nowinski, Virology, vol. 93, 1979, pp. 111–126.
Melchers ed., Lymph. Hybridomas, Current Topics in Micro & Immunol. Springer Verlag, NY, 1978, pp. IX–XIX.
Heilman, J of Virol., vol. 29, Jan. 1979, pp. 34–42.
Zweig, Virology, vol. 94, 1979, pp. 442–450.
Zweig, J of Virology, vol. 32, Nov. 1979, pp. 676–678.
Zweig, J of Virology, vol. 35, Sep. 1980.

*Primary Examiner*—Anna P. Fagelson
*Attorney, Agent, or Firm*—John S. Roberts, Jr.

[57] ABSTRACT

The method of producing clinical assays for use of monoclonal antibodies in the diagnosis of *Herpes simplex* virus (HSV) infections and the differentiation of *Herpes Simplex* virus types 1 and 2 as a diagnostic kit for differentiating HSV-1 and HSV-2 utilizing clone 1D4 against HSV-1 and clone 3E1 against HSV-2.

10 Claims, No Drawings

TEST METHODS EMPLOYING MONOCLONAL ANTIBODIES AGAINST *HERPES SIMPLEX* VIRUS TYPES 1 AND 2 NUCLEOCAPSIDS PROTEINS

This invention involves a process for developing monoclonal antibodies directed against antigenic determinants present on the 40,000 MW class of proteins associated with HSV type 1 and HSV type 2 nucleocapsids.

The present invention relates to a method of producing clinical assays for use of monoclonal antibodies in the diagnosis of *Herpes simplex* virus (HSV) infections and the differentiation of *Herpes simplex* virus types 1 and 2 as a diagnostic kit for differentiating HSV-1 and HSV-2 utilizing antibodies produced by clone 1D4 against HSV-1 and clone 3E1 against HSV-2.

One of the major problems in seroepidemiologic studies of *Herpes simplex* virus (HSV) infection is the differentiation of antibodies in human serum directed against HSV type 1 and type 2. It has been found that more than 80% of adults contain antibodies to HSV type 1, while a lower percent (10–20%) possess antibodies to HSV type 2. In modern medicine reliable methods are required for distinguishing between these antibodies in studies to determine whether one or both virus types are associated with a specific disease state. It is further noted that there is a possible relationship between HSV type 2 and cervical carcinoma. The present tests employed, which include microneutralization or crude radioimmunoprecipitation, are not sufficiently sensitive to differentiate between antibodies directed against the two types of *Herpes simplex* virus. By using the monospecific reagents or monoclonal reagents of the present invention prepared against both HSV type 1 and type 2, it is possible to differentiate between antibodies in human sera directed against the two HSV types by competition radioimmunoprecipitation (see Heilman et al, *J. Virol.* 29:34–42, 1979, post). In addition, studies have demonstrated that the monoclonal antibodies described in this invention can be employed for differentiating HSV type 1 and type 2 using immunofluorescence assays, immunoperoxidase assays, or enzyme-linked immunoabsorbant assays (ELISA).

A deposit of the 3E1 (hybridoma cells) and 1D4 (hybridoma cells) is available under American Type Culture Collection (ATCC) Accession Numbers HB 8067 and HB 8068, respectively. A deposit of said microorganisms 3E1 and 1D4 was made at the NIH Depository at Frederick, Maryland, as of Sept. 18, 1979, and converted to ATCC deposit as of June 9, 1981.

PRIOR ART STATEMENT

Heilman et al, *J. Virol.*, 29:34–42, 1979.
Zweig et al, *Virology*, 94:442–450, 1979.
Zweig et al, *J. Virol.*, 32:676–678, 1979.
Zweig et al, *J. Virol.*, 35 (in press).
Kohler et al, *Nature* (London), 256:495–496, 1975.
Kohler et al, *Eur. J. Immunol.*, 6:511–519, 1976.
Koprowski et al, *Proc. Natl. Acad. Sci. USA*, 74:2985–2988, 1977.
Martinis et al, *Proc. Natl. Acad. Sci. USA*, 75:2320–2323, 1978.
Nowinski et al, *Virology*, 93:111–126, 1979.

EXEMPLARY MATERIAL—GENERAL AND SPECIFIC

Preliminary studies have demonstrated that the p40 nucleocapsid proteins from HSV types 1 and 2 possess both type-specific and cross-reactive antigenic determinants (see Heilman et al, *J. Virol.*, 29:34–42, 1979). Monospecific antisera employed in the present studies were prepared by inoculating guinea pigs with fragments of SDS-polyacrylamide gels containing p40. The antisera so prepared contained both type-specific and cross-reactive antibodies as determined by radioimmunoassays. This itself was an advance that a single *Herpes simplex* virus protein contained multiple antigenic determinants, some of which were type-specific while others were cross-reactive. From this, experiments were undertaken to develop monoclonal antibodies with specificity directed against a single antigenic determinant expressed on HSV type 1 and type 2 p40 nucleocapsid proteins. The details of the procedures employed are described in the prior art statement and specially in Zweig et al, *J. Virol.*, 32:676–678, 1979. As a broad description, BALB/c mice were immunized with nucleocapsids purified from HSV type 1 or type 2 infected cells. The spleen and lymph nodes were removed and the cells were fused to BALB/c NSI/1 myeloma cells using polyethylene glycol 1500. Hybrid cells were selected by adding hypozanthine-amino-pterin-thymidine to the medium. The surviving cells in individual wells of microtiter plates were tested for antibody production, and those found positive were cloned and retested. One clonal isolate producing antibody against the p40 of HSV-1 (clone 1D4) and another clone producing antibody against the p40 of HSV type 2 (clone 3E1) were inoculated into mice pretreated with Pristane for production of ascites tumors. The ascites fluids were harvested and were tested by radioimmunoprecipitation and SDS-polyacrylamide gel analysis using extracts from HSV type 1 and type 2 infected cells. The results (see Zweig et al, *J. Virol.*, 32:676–678, 1979) indicated that clone 1D4 produced antibodies which reacted only with the p40 from HSV type 1, while clone 3E1 produced antibodies which reacted preferentially with the p40 from HSV type 2 infected cells. Using these reagents it was possible to specifically type HSV isolates as being either HSV type 1 or HSV type 2.

EXAMPLES

Example 1

Purification of Virions

Virions were purified essentially as described by Spear and Roizman, *J. Virol.*, 9:143–159, 1972. Cells infected with HSV-1 or HSV-2 were harvested 24 h post infection, suspended in 2 volumes of 1 mM dibasic sodium phosphate (pH 8.2) containing 0.1 mM phenylmethylsulfonyl fluoride, and allowed to swell for 10 min. at 0° C. The cells were disrupted by Dounce homogenization, and the nuclei were pelleted by centrifugation at 800×g for 10 min. and stored at −70° C. until used for the purification of nucleocapsids. Debris was removed from the cytoplasmic fraction by centrifugation in a Sorvall SS34 rotor at 8,000 rpm for 5 min. The virions in the cytoplasm were sedimented by centrifugation at 60,000×g for 1 h, suspended in 1 mM dibasic sodium phosphate, and subjected to sonic treatment. After incubation in the presence of DNase (50 μg/ml) and RNase (50 μg/ml) for 30 min. at room temperature, the virion samples were layered onto 34-ml 5 to 30% (wt/vol) dextran T10 (Pharmacia Fine Chemicals, Inc., Piscataway, N.J.) gradients in 1 mM dibasic sodium phosphate and centrifuged for 1 h at 20,000 rpm in a Beckman SW27 rotor. The virion-containing band was collected, diluted approximately fourfold with 10 mM Tris-hydrochloride (pH 7.6)-1 mM EDTA (TE buffer), and pelleted by centrifugation at 25,000 rpm for 1 h in a Beckman SW27 rotor. The virion pellet was suspended in a small volume of TE buffer and was layered onto an 11-ml 10 to 50% (wt/wt) potassium tartrate gradient in TE buffer. Centrifugation of the gradient was performed with a Beckman SW41 rotor for 2 h at 25,000 rpm. The virus band was collected, dialyzed against TE buffer, and stored at $-70°$ C.

Example 2

Radiolabeling of Cells

Cells were washed once with methionine-free Eagle minimal essential medium containing 5% dialyzed heat-inactivated fetal calf serum and then labeled with 100 $\mu$Ci of [$^{35}$S]methionine (800 to 1200 Ci/mmol; Amersham Corp., Arlington Heights, Ill.) per ml in the same methionine-free medium for 1 to 4 h. The cell sheet was then washed twice with ice cold Tris-buffered saline (pH 7.4) and scraped, and the cells were suspended in cold Tris-buffered saline. The cells were sedimented by centrifugation at 800×g for 10 min. and the cell pellets were stored at $-70°$ C. until used.

Example 3

Preparation of Cell Extracts and Disrupted Virus Particles for Immunoprecipitation Cell extracts were prepared by suspending the [$^{35}$S]methionine-labeled cells in buffer A (0.1 M Tris-hydrochloride [pH 8.0], 10% [vol, vol] glycerol, 0.5% Nonidet P-40, 0.5% sodium deoxycholate, 0.2 mM phenylmethylsulfonylfluoride) and incubating them for 1 h at 4° C. with shaking. The extracts were clarified by centrifugation at 60,000×g for 1 h [$^{35}$S]methionine-labeled virions and nucleocapsids were disrupted by heating at 100° C. for 5 min. in 0.5% sodium dodecyl sulfate (SDS)-2.5%. $\beta$-mercaptoethanol-0.05 M Tris-hydrochloride (pH 8.0), followed by a 10-fold dilution with buffer A.

Example 4

Reaction of Guinea Pig Antiserum with Purified Proteins

To verify that intracellular p40 and p80 possess common antigenic determinants, each protein class was purified from polyacrylamide gels and was successfully immunoprecipitated by guinea pig antiserum against nucleocapsid p40. Therefore, it is unlikely that the precipitation of intracellular p80 from infected cell extracts was due to specific or nonspecific binding to intracellular p40. Further, although the p40 protein exists in disulfide-linked complexes in nucleocapsids, soluble disulfide-linked complexes containing intracellular p40 or p80 were not detected by non-reducing SDS-polyacrylamide gel electrophoresis.

Example 5

Reaction of Monoclonal Antibodies with Infected Cell Extracts

Mouse hybrid cell lines which synthesize monoclonal antibodies against the p40 and p45 proteins of HSV-1 and HSV-2 nucleocapsids were established. Ascites fluids containing high titers of monoclonal antibodies were prepared and were reacted with extracts of cells infected with either HSV-1 or HSV-2. The anti-HSV-1 p40 monoclonal antibody produced by cell line 1D4 precipitated intracellular p40 and p80 from only HSV-1 infected cell extracts. In contrast, the anti-HSV-2 p40 monoclonal antibody produced by cell line 3E1 precipitated both HSV-1 and HSV-2 intracellular p40 and p80, although the homologous proteins were precipitated at higher dilutions of 3E1 antibody than were the heterologous proteins. Guinea pig antisera against the nucleocapsid p40 proteins of HSV-1 and HSV-2 also precipitated homologous proteins at higher antibody dilutions, but the differences in the dilutions which precipitated the homologous and heterologous proteins were not as great as the difference observed with the 3E1 monoclonal antibody.

Example 6

Reaction of Antibodies with Virion Proteins

Virions of HSV-1 and HSV-2 were purified from cytoplasmic extracts by centrifugation in dextran T10 and potassium tartrate gradients. Electron microscope observations indicated that the HSV-1 virion preparations contained about 10 to 15% unenveloped nucleocapsids, whereas the HSV-2 preparations contained as many as 50% unenveloped particles. These findings are reasonably consistent with those obtained by Cassai et al, *J. Virol.*, 16:1327–1331, 1975. Because of their higher purity, efforts were concentrated on analyzing preparations of HSV-1 virions to determine whether they possess polypeptides immunologically related to p40. Guinea pig antiserum and mouse monoclonal antibody against HSV-1 nucleocapsid p40 precipitated much smaller amounts of nucleocapsid p40 and p45 from virion preparations than from preparations of nucleocapsids, whereas a protein having the mobility of intracellular p80 was not precipitated from either virion or nucleocapsid preparations.

Example 7

Purification of Nucleocapsids

Nuclei of infected cells were suspended in about 2 volumes of 0.1 M Tris-hydrochloride (pH 8.0)—1.5 mM $MgCl_2$—0.1 mM phenylmethylsulfonyl fluoride. The nuclei were lysed by adding sodium deoxycholate to a final concentration of 0.5%, followed by sonic treatment. The nuclear lysates were incubated at room temperature for 30 min. in the presence of 50 $\mu$g of DNase per ml; this was followed by centrifugation at 8,000 rpm for 5 min. in a Sorvall SS34 rotor to remove debris. Nucleocapsids were purified from clarified nuclear lysates by centrifugation through 35% (wt/vol) sucrose, followed by centrifugation in a 10 to 40% (wt/wt) sucrose gradient.

We claim:

1. In a method of clinical testing and differentiating antibodies to *Herpes simplex* virus, HSV-1 and HSV-2, employing a competition immunoprecipitation, test, the improvement which comprises employing in said test as reagents monoclonal antibodies to the respective viruses HSV-1 and HSV-2 nucleocapsid p. 40 and p. 45 proteins of which antibodies are produced by hybrid cell lines ID4 (HSV-1) and 3EI (HSV-2).

2. The method of claim 1 wherein the test is competition radioimmuno precipitation.

3. In a method of clinical testing and differentiating antibodies to *Herpes simplex* virus, HSV-1 and HSV-2, employing the enzyme-linked immunoabsorbent assay, the improvement which comprises employing in said test as reagents monoclonal antibodies to the respective viruses HSV-1 and HSV-2 nucleocapsid p. 40 and p. 45 proteins which antibodies are produced by hybrid cell lines ID- (HSV-1) and 3EI(HSV-2).

4. The method of claim 3 wherein the enzyme is peroxidase.

5. The method of testing and differentiating *Herpes simplex* virus, HSV-1 and HSV-2, in a test sample which comprises reacting the infected samples with monoclonal antibodies against the nucleocapsid p. 40 and p. 45 proteins of HSV-1 and HSV-2, respectively, and noting the reaction thereof by immuno-peroxidase assay, immunofluorescence assay, enzyme-linked immunoabsorbent assay immunoprecipitation assay, or radioimmunoassay.

6. The method of claim 5 wherein the test is an immunoperoxidase assay.

7. The method of claim 5 wherein the test is an radioimmunoassay.

8. The method of claim 5 wherein the test is an enzyme-linked immunoabsorbent assay.

9. The method of claim 5 wherein the test is an immunofluorescence assay.

10. The method of claim 5 wherein the test is an immunoprecipitation assay.

* * * * *